United States Patent
Wagner et al.

(10) Patent No.: US 10,807,018 B2
(45) Date of Patent: Oct. 20, 2020

(54) PROCESS FOR PURIFICATION OF AN ORGANIC COMPOSITION

(71) Applicant: BASF SE, Ludwigshafen (DE)

(72) Inventors: Hans-Guenter Wagner, Neuleiningen (DE); Christoph Bayer, Nuremberg (DE); Lothar Karrer, Pfungstadt (DE); Markus Eggersmann, Speyer (DE); Sven Crone, Limburgerhof (DE); Kam Wing Wong, Tsuen Wang (DE); Heinz Ruetter, Xanten (DE); Patrik Pietz, Shanghai (CN)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/517,558

(22) PCT Filed: Oct. 9, 2014

(86) PCT No.: PCT/CN2014/088223
§ 371 (c)(1),
(2) Date: Apr. 7, 2017

(87) PCT Pub. No.: WO2016/054785
PCT Pub. Date: Apr. 14, 2016

(65) Prior Publication Data
US 2017/0259188 A1   Sep. 14, 2017

(51) Int. Cl.
*B01D 15/00*   (2006.01)
*C10G 50/00*   (2006.01)
(Continued)

(52) U.S. Cl.
CPC ............ *B01D 15/00* (2013.01); *B01D 3/14* (2013.01); *C07C 2/06* (2013.01); *C07C 5/03* (2013.01);
(Continued)

(58) Field of Classification Search
CPC .................. B01D 15/00; B01D 2259/40086; C07C 2/06; C07C 5/03
(Continued)

(56) References Cited

U.S. PATENT DOCUMENTS 4,814,517 A * 3/1989 Trubac .................. C07C 41/36
568/697
4,935,399 A 6/1990 Blackburn et al.
(Continued)

FOREIGN PATENT DOCUMENTS

DE  10 2008 007 081 A1  8/2009
FR       2988398 A1 *  9/2013
(Continued)

OTHER PUBLICATIONS

International Search Report dated Jun. 12, 2015 in PCT/CN2014/088223.
(Continued)

Primary Examiner — In Suk C Bullock
Assistant Examiner — Jason Y Chong
(74) Attorney, Agent, or Firm — Oblon, McClelland, Maier & Neustadt, L.L.P.

(57) ABSTRACT

Disclosed is a process for the purification of an organic composition (OC1) by adsorption using an assembly containing at least two adsorbers. The organic composition (OC1) comprising at least one alkane, at least one olefin and at least one compound containing oxygen and/or sulphur is fed into a first adsorber (A1) of the assembly in order to obtain an organic composition (OC2) comprising at least one alkane, at least one olefin and a reduced amount of at least one compound containing oxygen and/or sulphur compared to the respective amount in organic composition (OC1). Hydrogenation of the organic composition (OC2) provides a stream (S2) comprising at least one alkane and a
(Continued)

Figure 1:
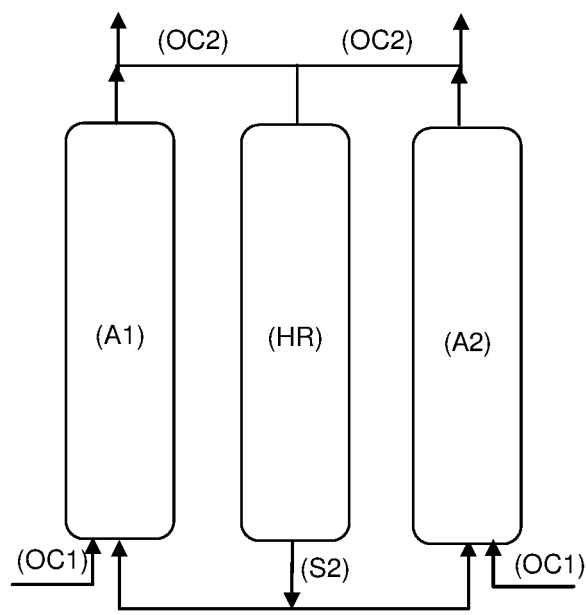

reduced amount of at least one olefin compared to the respective amount in organic composition (OC2) obtained after feeding into the first adsorber (A1). A second adsorber (A2) of the assembly is regenerated by contact with stream (S2).

20 Claims, 2 Drawing Sheets

(51) Int. Cl.
| | |
|---|---|
| C10G 25/12 | (2006.01) |
| C10G 57/02 | (2006.01) |
| C10G 45/00 | (2006.01) |
| C10G 25/00 | (2006.01) |
| C10G 67/06 | (2006.01) |
| C10G 69/12 | (2006.01) |
| B01D 3/14 | (2006.01) |
| C07C 2/06 | (2006.01) |
| C07C 5/03 | (2006.01) |

(52) U.S. Cl.
CPC ............. *C10G 25/00* (2013.01); *C10G 25/12* (2013.01); *C10G 45/00* (2013.01); *C10G 50/00* (2013.01); *C10G 57/02* (2013.01); *C10G 67/06* (2013.01); *C10G 69/126* (2013.01)

(58) Field of Classification Search
USPC ....... 585/255, 820, 800, 826, 502, 500, 512, 585/258, 250
See application file for complete search history.

(56) References Cited

U.S. PATENT DOCUMENTS

| | | | |
|---|---|---|---|
| 4,935,400 A | 6/1990 | Blackburn et al. | |
| 4,952,746 A | 8/1990 | Johnson et al. | |
| 5,177,298 A | 1/1993 | Yon et al. | |
| 5,237,111 A * | 8/1993 | Yon | C07C 41/36 568/697 |
| 5,288,370 A * | 2/1994 | Asselineau | C07C 7/08 203/51 |
| 6,281,397 B1 * | 8/2001 | Santi | B01J 31/0212 585/250 |
| 6,657,090 B2 * | 12/2003 | Rix | B01D 3/009 208/16 |
| 6,673,239 B2 | 1/2004 | Johnson et al. | |
| 2005/0075528 A1 | 4/2005 | Burkhardt et al. | |
| 2007/0123743 A1 | 5/2007 | Ng et al. | |
| 2008/0200745 A1 | 8/2008 | Sigl et al. | |
| 2011/0200507 A1 | 8/2011 | Steiner et al. | |
| 2011/0301398 A1 * | 12/2011 | Heidemann | C07C 2/10 585/512 |
| 2012/0024324 A1 | 2/2012 | Force et al. | |
| 2013/0131416 A1 * | 5/2013 | Crone | C07C 2/06 585/329 |
| 2015/0065765 A1 * | 3/2015 | Villechange | C10G 25/00 585/254 |

FOREIGN PATENT DOCUMENTS

| | | |
|---|---|---|
| WO | WO 00/20359 A1 | 4/2000 |
| WO | WO 01/83407 A1 | 11/2001 |
| WO | WO 2005/056503 A1 | 6/2005 |
| WO | WO 2006/089956 A2 | 8/2006 |
| WO | WO 2010/023249 A1 | 3/2010 |
| WO | WO 2010/057905 A1 | 5/2010 |
| WO | WO 2012/004328 A1 | 1/2012 |
| WO | WO 2016/054785 A1 | 4/2016 |
| WO | WO 2016/054786 A1 | 4/2016 |
| WO | WO 2016/054787 A1 | 4/2016 |
| WO | WO 2016/054788 A1 | 4/2016 |
| WO | WO 2016/054789 A1 | 4/2016 |
| WO | WO 2016/054790 A1 | 4/2016 |

OTHER PUBLICATIONS

International Preliminary Report on Patentability and Written Opinion dated Apr. 11, 2017 in PCT/CN2014/088223.
European Office Action dated May 23, 2018 in Patent Application No. 14903568.5.
Extended European Search Report dated May 3, 2018 in corresponding European Patent Application No. 14903568.5, 3 pages.

* cited by examiner

PROCESS FOR PURIFICATION OF AN ORGANIC COMPOSITION

The invention relates to a process for the purification of an organic composition (OC1) by adsorption using an assembly containing at least two adsorbers. The organic composition (OC1) comprising at least one alkane, at least one olefin and at least one compound containing oxygen and/or sulphur is fed into a first adsorber (A1) of the assembly in order to obtain an organic composition (OC2) comprising at least one alkane, at least one olefin and a reduced amount of at least one compound containing oxygen and/or sulphur compared to the respective amount in organic composition (OC1). Hydrogenation of the organic composition (OC2) provides a stream (S2) comprising at least one alkane and a reduced amount of at least one olefin compared to the respective amount in organic composition (OC2) obtained after feeding into the first adsorber (A1). A second adsorber (A2) of the assembly is regenerated by contact with stream (S2).

Technical organic compositions often need to be purified from compounds containing heteroatoms in particular heteroatoms like sulphur and/or oxygen before use as starting materials in catalyzed reactions. These impurities may inhibit or lower the activities of catalysts. The purification can be performed by employing adsorbers.

WO 2010/057905 A1 discloses a process for the oligomerization of olefins by bringing at least one C2 to C8 olefin into contact with a nickel containing heterogeneous catalyst. Preferably the olefins are passed over an adsorption material before being brought in contact with the catalyst in order to prevent catalyst poisoning. However, WO 2010/057905 A1 does not disclose a process for the regeneration of adsorbers.

DE 10 2008 007 081 A1 discloses a process for the production of n-butene-oligomers and 1-butene from a technical mixture-I of $C_4$-hydrocarbons. Analogously to WO 2010/057905 A1, the document mentions the need for the removal of certain compounds containing heteroatoms out of the hydrocarbon mixture intended to be used in the catalyzed oligomerization process. The document does not disclose a process for the regeneration of adsorbers.

WO 2005/056503 discloses a composite catalyst for the selective oligomerization of lower alkenes and the production of high octane products. While the oligomerization of lower alkenes and mixtures of alkenes is reported in detail, the use of adsorbers for purification of the starting materials or the regeneration of adsorbers is not mentioned.

WO 01/83407 describes a process for the oligomerization of alkenes having from 3 to 6 carbon atoms using a catalyst containing a zeolite of the MFS structure type under conditions to obtain selectively oligomeric product containing predominant amount of certain oligomers. Like in the previously discussed document of prior art neither the use of adsorbers for purification of starting materials nor their regeneration is part of the disclosure.

In order to remove the adsorbed compounds containing heteroatoms the regeneration of the adsorbers is required periodically. This can be achieved, for example, by purging the adsorber with inert gases or hydrocarbons at elevated temperatures. Suitable regeneration media need to be essentially free of olefins and compounds containing heteroatoms, in particular free of compounds containing oxygen and/or sulphur. Residual olefins tend to form detrimental coke and polymer precipitates on the adsorbent, at the temperatures applied, during the regeneration process.

Technical organic compositions comprising olefins purified in an adsorber often comprise significant amounts of saturated hydrocarbons. These purified saturated hydrocarbons may be separated from the olefins in downstream process steps and would be applicable for the regeneration of the adsorbers. However, even after distillation of the product stream, the saturated hydrocarbon fraction usually still contains considerable amounts of residual olefins. Streams containing considerable amounts of olefins cannot successfully be employed for adsorber regeneration due to the increased formation of precipitates and/or coke on the adsorber surface.

U.S. Pat. No. 4,935,399 and U.S. Pat. No. 4,935,400 both describe a similar process for the reduction of hydrocarbon losses during regeneration of adsorbers containing molecular sieves for the removal of sulphur compounds from liquid hydrocarbon streams. While the process according to U.S. Pat. No. 4,935,399 comprises heating of the adsorber bed directly by a device located within the adsorber bed, in U.S. Pat. No. 4,935,400 the adsorber bed is heated by purging with gaseous hydrocarbon only. Both documents explain the use of hydrocarbon streams for the regeneration of adsorber beds containing molecular sieves, but none of them deals with a hydrogenation step.

U.S. Pat. No. 5,177,298 discloses a process for regeneration of oxygenate-containing adsorbents using hydrocarbon regenerant streams. The streams used require extra pretreatment by additional adsorbers in order to remove compounds containing sulphur or oxygen. Furthermore, U.S. Pat. No. 5,177,298 does not disclose a hydrogenation step.

U.S. Pat. No. 6,673,239 B2 discloses a system and process for removing water and compounds containing heteroatoms from hydrocarbons and a system and process for regeneration of adsorbents used therein. The regeneration comprises passing an isoparaffin over a water-adsorbent, then passing the isoparaffin in over the heteroatom-containing compound adsorbent. However, U.S. Pat. No. 6,673,239 B2, does not deal with a hydrogenation step.

US 2012/0024324 A1 discloses a process for regeneration of purification beds with a jet compressor in an open loop cycle. A fluid composition comprising an inert gas and a regeneration composition is used as regeneration media. Apart from hydrogen as possible secondary component, further constituents of the fluid composition are not defined. In particular the application of hydrocarbons as regeneration media is not considered in the disclosure.

The problem underlying the present invention consists in the development of a new process for the purification of an organic composition.

The object is achieved by a process for the purification of an organic composition (OC1) by adsorption using an assembly containing at least two adsorbers comprising the following steps a) to c):

a) the organic composition (OC1) comprising at least one alkane and/or at least one olefin and at least one compound containing oxygen and/or sulphur is fed into a first adsorber (A1) of the assembly in order to obtain an organic composition (OC2) comprising at least one alkane, at least one olefin and a reduced amount of at least one compound containing oxygen and/or sulphur compared to the respective amount in organic composition (OC1), b) hydrogenation of at least a part of the organic composition (OC2) obtained in step a) to obtain a stream (S2) comprising at least one alkane and a reduced amount of at least one olefin compared to the respective amount in organic composition (OC2), c) regenerating a second adsorber (A2) of the assembly by contact with stream (S2) obtained in step b), wherein the purification employing the first adsorber (A1) of the assembly according to step a) and the regeneration of the second adsorber (A2) of the assembly according to step c) are run in parallel.

Using adsorbers for purification of organic composition, efficient adsorber regeneration is required in order to keep the overall throughput high. This is of particular importance if the organic composition to be purified comprises relatively high amounts of compounds to be adsorbed, e.g. compounds containing oxygen and/or sulphur. The invention allows short regeneration times, equal to purification time, even for organic compositions with high amounts of impurities. Furthermore, the devices used can be kept small relative to the load of impurities.

Another advantage of the present invention can be seen in the fact that the invention allows the operation of at least one adsorber in regeneration mode parallel to the operation of at least one other adsorber in operation mode in the same plant. In combination with the possible application of equal times for regeneration and operation mode delays in the process or idling times are minimized.

Hydrocarbons comprising residual olefins, corresponding to stream (S2) within the context of the present invention, can be applied for adsorber regeneration, without significant formation of detrimental precipitates of coke and polymers on the adsorbent. Within the context of the present invention, the stream (S2) is being employed as regeneration stream or regeneration media of an adsorber.

The stream (S2) originates from an earlier process step. Thus, the present invention allows the employment of components as regeneration media for an adsorber whereby said components have been purified earlier on the same adsorber, but who are in fact by-products, for example, within a process for producing octene by dimerization of butene. Such by-products are usually discharged as waste, but within the process of the present invention they can be successfully employed/converted into a regeneration stream.

Compared to other processes of prior art, no additional purification step to remove compounds containing sulphur and/or oxygen or other heteroatoms is required since these hydrocarbon mixtures are obtained for example as by-products during purification of technical organic compositions comprising olefins by means of adsorbers. The purchase of alternative regeneration media like inert gases is therefore avoided.

It is also an advantage that according to another embodiment of the invention it is possible to collect and to recycle residual organic composition remained in the pores of the adsorber after finishing the operation mode to further reduce losses of valuable organic intermediate.

In summary, operating costs and environmental burden are lowered by reduction of energy consumption, waste, recovery of product and recycling of by-product as regeneration media due to a combination of advantageous measures implemented in the present invention.

The invention is specified in more detail as follows:

The invention relates to a process for the purification of an organic composition (OC1) by adsorption using an assembly containing at least two adsorbers comprising the following steps a) to c):

Within the context of the present invention, the term "adsorber" comprises the adsorbent as well as the device in which the adsorbent is embedded in. Instead of the term "adsorbent" the expression "adsorber material" may be used. The term adsorber may be used equivalently for adsorbent, even if a certain statement actually refers only to the adsorbent but not to the device in which the adsorbent is embedded in.

The adsorbers can be employed for the adsorption of compounds containing oxygen and/or sulphur out of organic compositions. Preferably, the adsorbers can be employed for the adsorption of ethers, alcohols, thiols, thioethers, sulfoxides, ketones, aldehydes or mixtures thereof.

Any adsorbent known to the person skilled in the art being appropriate for performing the adsorption of compounds containing oxygen and/or sulphur out of organic compositions may be applied.

Preferred adsorbents are, for example, molecular sieves with a pore diameter of 4 to 15 Å. Further, molecular sieves applicable are crystalline, natural aluminia silicates, like layer lattice silicates or synthetic molecular sieves. Furthermore, commercially available molecular sieves as sold by the Bayer AG, Dow, Union Carbide, Laporte or Mobil may be used. These molecular sieves can be, for example, zeolites of the A-, X- and Y-type. Moreover, synthetic molecular sieves comprise silicon and aluminum as main components, whereby other atoms as side-components such as lanthanides like gallium, indium and lanthanum or other elements like nickel, cobalt, copper, zinc or silver may be useful. These can be introduced into the zeolites for example by means of an ion-exchange with exchangeable cations.

Likewise, synthetic zeolites can be employed, in which other atoms like boron or phosphorus are incorporated in the layer by co-precipitation.

Further suitable adsorbents are aluminum phosphate, silicon dioxide, kieselgur, titanium dioxide, zirconium dioxide, polymeric adsorbents and mixtures thereof.

The most preferred adsorbent is aluminum oxide, commercially available for example as Selexsorb CDL from BASF.

Preferably the at least two adsorbers (A1) and (A2) are based on a molecular sieve or aluminum oxide, preferably aluminum oxide and/or the adsorbers can be employed for the adsorption of compounds containing oxygen and/or sulphur out of organic compositions, preferably the adsorbers can be employed for the adsorption of ethers, alcohols, thiols, thioethers, sulfoxides, ketones, aldehydes or mixtures thereof.

In step a) the organic composition (OC1) comprising at least one alkane and/or at least one olefin and at least one compound containing oxygen and/or sulphur is fed into a first adsorber (A1) of the assembly in order to obtain an organic composition (OC2) comprising at least one alkane, at least one olefin and a reduced amount of at least one compound containing oxygen and/or sulphur compared to the respective amount in organic composition (OC1).

Preferably the alkane contains 1 to 14, more preferably 3 to 10, most preferably 4 to 6 carbon atoms in its longest chain.

The at least one alkane can be, for example, linear, branched and/or cyclic and is selected from the group: methane, ethane, propane, butane, pentane, hexane, heptane, octane, nonane and decane. Preferably the at least one alkane is butane.

In the context of the present invention, if not stated otherwise, it is not differentiated between the different isomers of a certain alkane. For example, the term butane may refer to n-butane and/or isobutane.

The organic compositions, within this invention, may comprise in a specific embodiment one or more further alkanes different from butane, which may be selected from the same alkanes as specified above.

Preferably the organic composition (OC1) comprises butane and butene.

Preferably the organic composition (OC1) comprises at most 1000 wt-ppm, more preferably at most 300 wt-ppm, most preferably at most 200 wt-ppm of at least one compound containing oxygen and/or sulphur.

The organic composition (OC1) preferably comprises at least 15 wt-ppm of at least one compound containing oxygen and/or sulphur.

Preferably organic composition (OC1) comprises not more than 250 wt-ppm 1,2-dimethoxyethane (DME), not more than 150 wt-ppm methyl tertiary butyl ether (MTBE), not more than 50 wt-ppm acetone, not more than 50 wt-ppm methanol and/or not more than 50 wt-ppm methyl mercaptane.

The at least one olefin may comprise at least one linear, branched, cyclic monoolefin and/or at least one linear, branched, cyclic olefin containing more than one olefinic double bond. Preferably the olefin has 2 to 14, more preferably 3 to 10, most preferably 4 to 6 carbon atoms in its longest carbon chain.

If more than one stereoisomer of an olefin exists, e.g. the corresponding cis- and trans-isomer, these isomers are, in the context of the present invention, regarded as equivalent. Further, it is not differentiated between constitutional isomers of monoolefins. For example, the term butene may comprise the constitutional isomers 1-butene and/or 2-butene as well as 2-butene the corresponding cis- and/or trans-stereoisomer.

Monoolefins can be, for example, selected from the group: ethene, propene, butene pentene, hexene, heptene, octene, nonene and decene. Preferably, the olefin is butene.

If at least one olefin containing more than one olefinic double bond is present, this olefin is preferably a diene, more preferably butadiene.

The organic compositions comprising at least one olefin may comprise in a specific embodiment one or more further olefins different from butene which may be selected from the same olefins as specified above.

The organic composition (OC1) may comprise at least 20 wt-% of the at least one olefin, preferably butene and/or at least 20 wt-% of the at least one alkane, preferably butane.

Preferably in the organic composition (OC1) the ratio of alkane to olefin is 0.5:1 to 2:1 [weight-%:weight-%].

The organic composition (OC2) preferably comprises not more than 20 wt-ppm of compounds containing oxygen and/or sulphur.

Preferably the load of the adsorber (A1) with organic composition (OC1) in step a) is 10 to 100 t/h, more preferably 30 to 80 t/h, most preferably 45 to 65 t/h.

Preferably the organic composition (OC1) is fed into the adsorber (A1) in step a) at a temperature of 25 to 40° C.

Preferably the organic composition (OC1) is fed into the adsorber (A1) in step a) at a pressure of 5 to 8 bar.

In step b) at least a part of the organic composition (OC2) obtained in step a) is hydrogenated to obtain a stream (S2) comprising at least one alkane and a reduced amount of at least one olefin compared to the respective amount in organic composition (OC2).

The hydrogenation may be carried out by any appropriate method known to the person skilled in the art.

Useful may be a catalyzed hydrogenation using at least a catalyst and a hydrogen source.

Preferably, the catalyst comprises d-block elements, more preferably, for example, Pd, Pt, Ru, Ir, Rh, Cu, Ni or Co, most preferably Pd, Ni, Pt or Rh, in particular preferably Pd or Ni.

The hydrogenation can be performed using $H_2$-gas and/or as catalytic transfer hydrogenation, employing for example ammonium formate, silyl hydrides, $NaBH_4$, cyclohexene or alcohols like methanol and propanol as hydrogen source. Preferably, the hydrogenation is carried out using $H_2$-gas as hydrogen source.

The hydrogen source and the solvent may be identical, for example, in the case of alcohols like methanol.

Any solvent known to the person skilled in the art being appropriate for performing the hydrogenation may be employed.

In general polar-protic, polar-nonprotic and/or unpolar solvents can be employed, for example methanol, ethanol, propanol, isopropanol, tetrahydrofurane or toluene.

Alternatively, the hydrogenation can be carried out without using any solvent.

In a preferred embodiment, the hydrogenation is carried out without the use of any solvent and with $H_2$-gas as hydrogen source.

Any reactor known to the person skilled in the art being appropriate for performing the hydrogenation may be employed.

Preferably a trickle bed reactor is employed for performing the hydrogenation.

Preferably the stream (S2) comprises not more than 1000 wt-ppm olefin, more preferably not more than 500 wt-ppm olefin, most preferably not more than 100 wt-ppm olefin, preferably the olefin is butene.

Preferably the stream (S2) comprises at least 99 wt-% of at least one alkane, more preferably at least 99.5 wt-% of at least one alkane, most preferably at least 99.9 wt-% of at least one alkane, preferably the alkane is butane.

Preferably the stream (S2) comprises ≤20 wt-ppm, more preferably ≤5 wt-ppm, most preferably ≤1 wt-ppm of at least one compound containing oxygen and/or sulphur.

The respective organic composition subjected to hydrogenation in step b) preferably comprises butane and butene, more preferably at least 96 wt-% butane and not more than 4 wt-% butene.

The respective organic composition subjected to hydrogenation in step b) preferably comprises ≤20 wt-ppm, more preferably ≤5 wt-ppm, most preferably ≤1 wt-ppm of at least one compound containing oxygen and/or sulphur.

In step c) a second adsorber (A2) of the assembly is regenerated by contact with stream (S2) obtained in step b), wherein the purification employing the first adsorber (A1) of the assembly according to step a) and the regeneration of the second adsorber (A2) of the assembly according to step c) are run in parallel.

Regeneration, in the context of the present invention, means desorption and removal of adsorbed compounds containing oxygen and/or sulphur from the adsorber, in particular from the adsorbent in the adsorber. Regeneration of the adsorber may also comprise additional measures/steps necessary, for example, for preparation of the regeneration medium, the adsorber itself for regeneration or for enabling the adsorber after finished regeneration to be operated again for adsorption of compounds containing oxygen and/or sulphur out of organic compositions.

Consequently, an adsorber, within this invention, can at least be operated in the modes of operation: operation mode or regeneration mode.

An adsorber, within this invention, is in operation mode, when a stream comprising an organic composition, comprising at least one alkane and/or at least one olefin and compounds containing oxygen and/or sulphur, preferably not being routed through the adsorber before, is fed into the adsorber and compounds containing oxygen and/or sulphur are adsorbed completely or at least partially from this stream on the adsorbent.

Preferably at least 50%, more preferably at least 80%, most preferably at least 97% of the compounds containing oxygen and/or sulphur are adsorbed from the stream comprising organic composition, according to the preceding paragraph.

An adsorber, within this invention, is in regeneration mode when measures to remove or measures related to the removal of adsorbed compounds containing oxygen and/or sulphur from the adsorbent are carried out or optionally the definition of the operation mode does not apply.

Preferably the time for regeneration and purification is equal, more preferably in the range of 12 to 48 h.

In a further embodiment the invention comprises at least one, of the following options i) to viii):
- i) the respective organic composition subjected to hydrogenation in step b) comprises butane and butene, preferably at least 96 wt-% butane and not more than 4 wt-% butene, and/or
- ii) the respective organic composition subjected to hydrogenation in step b) comprises ≤20 wt-ppm, preferably ≤5 wt-ppm, more preferably ≤1 wt-ppm of at least one compound containing oxygen and/or sulphur, and/or
- iii) the stream (S2) comprises not more than 1000 wt-ppm olefin, preferably not more than 500 wt-ppm olefin, most preferably not more than 100 wt-ppm olefin, preferably the olefin is butene, and/or
- iv) the stream (S2) comprises at least 99 wt-% of at least one alkane, preferably at least 99.5 wt-% of at least one alkane, most preferably at least 99.9 wt-% of at least one alkane, preferably the alkane is butane and/or
- v) the stream (S2) comprises ≤20-wt-ppm, preferably ≤5 wt-ppm, more preferably ≤1 wt-ppm of at least one compound containing oxygen and/or sulphur, and/or
- vi) the load of the adsorber (A1) with organic composition (OC1) in step a) is 10 to 100 t/h, preferably 30 to 80 t/h, more preferably 45 to 65 t/h and/or
- vii) the organic composition (OC1) is fed into the adsorber (A1) in step a) at a temperature of 25 to 40° C., and/or
- viii) the organic composition (OC1) is fed into the adsorber (A1) in step a) at a pressure of 5 to 8 bar.

Step c) of the process according to the present invention may comprise at least one of the following component steps c1) to c6):
- c1) converting stream (S2) from liquid into gaseous phase,
- c2) heating the adsorber by contact with the gaseous stream (S2), wherein the gaseous stream (S2) is condensed within the adsorber,
- c3) heating the adsorber by contact with the gaseous stream (S2) up to a temperature in the range of 230 to 270° C. without any condensation of the gaseous stream (S2) within the adsorber,
- c4) regeneration of the adsorber at a temperature in the range of 230 to 270° C. by contact with the gaseous stream (S2),
- c5) cooling of the adsorber by contact with the gaseous stream (S2) to a temperature in the range of 80° C. to 120° C., and/or
- c6) cooling of the adsorber by contact with the liquid stream (S2) obtained in step a) to a temperature below 80° C., preferably to a temperature in the range of 40 to 60° C., preferably step d) (as defined below) is carried out prior to step c) and step c) comprises the component steps c1), followed by c2), followed by c3), followed by c4), followed by c5) and followed by c6).

The conversion of liquid stream (S2) into gaseous phase in step c1) may be carried out by lowering the pressure and/or heating of the liquid stream (S2), preferably by employing at least one evaporator and/or at least one super-heater and/or at least one flash vessel.

In a preferred embodiment, liquid stream (S2), with a pressure of 5 to 80 bar, preferably of 10 to 50 bar, most preferably of 20 to 30 bar is, for the conversion according step c1), fed into a flash vessel, wherein the pressure of liquid stream (S2) is lowered to 4 to 16 bar, preferably to 7 to 13 bar, most preferably to 8 to 11 bar.

Lowering the pressure of liquid stream (S2), preferably in a flash vessel, compared to the pressure of liquid (S2) fed into the flash vessel, can result in conversion of at least a part of liquid stream (S2) into gaseous phase. Remaining liquid stream (S2) at lowered pressure may be converted into gaseous phase by use of at least one evaporator.

By lowering the pressure of liquid stream (S2), preferably in a flash vessel, compared to the pressure of liquid stream (S2) obtained in step a), 0 to 80%, preferably less than 10% of liquid stream (S2) may be converted into gaseous phase.

Alternatively, liquid stream (S2) may be converted into gaseous phase, preferably with at least one evaporator, without prior lowering the pressure.

Within the present invention, an evaporator is a device which converts a liquid stream into gaseous phase by transfer of heat to the liquid stream.

It is also possible to use two or more evaporators through which stream (S2) may flow in series and/or in parallel.

Any evaporator known to the person skilled in the art being appropriate for performing the evaporation may be applied.

Examples for evaporators are electric evaporators and evaporators transferring heat by means of a heat transfer medium, like steam (gaseous water) or other gaseous media, hydrocarbons, oils or salts. Preferably, the evaporators are of the Kettle type.

The conversion of liquid stream (S2) into gaseous phase according to step c1) may also comprise super-heating.

Super-heating, in the context of the present invention, means further increasing the temperature of the already gaseous stream (S2), preferably by transfer of heat to the gaseous stream (S2).

Any super-heater known to the person skilled in the art being appropriate for the super-heating may be applied.

Super-heating may be performed with one or more super-heaters. When more than one super-heater is used, the super-heaters can be arranged in series and/or in parallel.

Examples for possible super-heaters are electric super-heaters and super-heaters transferring heat by means of a heat transfer medium, suitable gaseous media, hydrocarbons, oils or salts. Preferably, super-heaters are of the shell-and-tube type.

Evaporating and super-heating may be performed in different devices and/or be combined in at least one device capable to fulfill both functions, for instance a shell-and-tube heat exchanger stacked on top of a Kettle-type evaporator.

If evaporators and/or super-heaters based on a heat transfer medium are used, the same stream of heat transfer medium may be passed through only one evaporator or super-heater or through more than one evaporator or superheater. The same stream of heat transfer medium can be used for evaporators or super-heaters or for evaporators and super-heaters.

The same type of heat transfer medium can be applied for all evaporators and/or super-heaters or different types of heat transfer media for each individual device or a group of evaporators and/or super-heaters may be used.

Dependent on the temperature actually required at a given time of the process, the heat transfer to the liquid or gaseous stream (S2) by the respective evaporators and/or super-heaters may be reduced, stopped completely and/or one or any number of evaporators and/or one or any number of super-heaters may be by-passed by stream (S2).

Preferably gaseous stream (S2) is passed through all super-heaters and heat transfer is reduced or stopped when lower temperatures for gaseous stream (S2) are required.

Preferably evaporators and/or super-heaters are by-passed if liquid stream (S2) is required.

Condensation, meaning conversion from gaseous into liquid phase, of the components comprised in stream (S2) in step c), in particular in step c2), usually takes place if at least one spot, meaning spacial element, inside the adsorber, being the adsorbent and/or the adsorber wall, has a temperature, which is below the dew point temperature of the respective components comprised in gaseous stream (S2), present at that spot.

The pressure in the adsorber (A1) and/or (A2), being in regeneration mode, is usually defined by the pressure of stream (S2) in the respective adsorber.

In another embodiment of the invention, the condensate obtained in step c2) contains the stream (S2) and the residue of the organic composition (OC1) and/or (OC2) which was not removed from the adsorber (A2) when carrying out draining step d), and the condensate is optionally collected in a device, preferably in a buffer vessel, in order to pass the collected condensate through an adsorber during its operation mode.

An additional draining step d), prior to carrying out step c) may be carried out in order to at least partially remove an organic composition (OC1) and/or (OC2) which was passed through the second adsorber during its operation mode.

Preferably at least 10%, more preferably at least 30%, most preferably at least 40% of the organic composition (OC1) and/or (OC2) is removed from the adsorber in the draining step d).

Prior to step b), an additional step e) may be carried out, comprising:

e) oligomerization of organic composition (OC2), wherein at least one of the olefins is at least partially oligomerized, obtaining an organic composition (OC3) comprising a reduced amount of at least one olefin and an increased amount of at least one oligomerized olefin compared to the respective amounts in (OC2), with use of (OC3) rather than (OC2) in the subsequent steps.

preferably the oligomerization is a dimerization and more preferably butene is at least partially dimerized to octene.

Oligomerization, within the present invention, is defined as a catalyzed chemical reaction, in which at least two olefins are connected to an oligomerized olefin, with a higher molecular weight than each of the at least two olefins connected, over a newly formed single bond and wherein at least one double bond of the at least two olefins, per newly formed connecting single bond in the oligomerized olefin, is transformed into a single bond.

If not more than two olefins per oligomerized olefin were connected, for this reaction the term dimerization may be used.

It is not differentiated between constitutional and stereoisomers of the oligomerized olefins.

Preferably the at least one oligomerized olefin has a higher molecular weight, than the at least one olefin from organic compositions originating from and/or being fed into steps preceding step b).

Preferably the at least one oligomerized olefin is octene.

Preferably at least 10 wt.-%, more preferably at least 20 wt.-% of the at least one olefin of (OC2) is oligomerized.

The oligomerization according to step e) may be carried out i) with a catalyst comprising 10 bis 70 wt.-% NiO, 5 to 30 wt.-% $TiO_2$ and/or $ZrO_2$, 0 to 20 wt.-% AlO, 20 to 40 wt.-% $SiO_2$ and 0.01 to 1 wt.-% of an alkali metal oxide, preferably the catalyst comprises at least 50 wt.-% NiO and 0 wt.-% Al and/or ii) at a pressure of 10 to 300 bar, preferably 10 to 50 bar, most preferably at pressure of 10 to <30 bar and/or iii) at a temperature of 20 to 280° C., preferably at a temperature of 30 to 130° C. and/or iv) adiabatically, without additional measures taken for cooling by means of an heat exchange medium and/or v) in a fixed bed process.

The organic composition (OC3) preferably comprises octene.

Organic composition (OC3) preferably comprises at least one alkane.

Organic composition (OC3) preferably comprises at least 5 wt.-% of octene.

The organic composition (OC3) preferably comprises not more than 5 wt.-ppm of compounds containing oxygen and/or sulphur.

In a preferred embodiment of the invention, i) the oligomerization according to step b) is a dimerization and/or ii) the olefin in the organic composition (OC2) is butene, which is at least partially dimerized to octene.

Preferably at least 10 wt.-%, more preferably at least 20 wt.-%, of the butene in the organic composition (OC2) is dimerized to octene.

In a further embodiment of the invention step e) and f) (as defined below) are carried out more than one time during the process.

In this embodiment, the oligomerized olefins are separated from the organic composition obtained comprising the application of step f) after finishing a step according to step e). In the following step e), the corresponding organic composition obtained from the upper part of the distillation column in step f) is reused instead of (OC2). In the respective next step following the last, step b) is carried out, whereby the organic composition corresponding to (OC3) is applied.

Preferably step e), in the embodiment as specified in the preceding paragraph, is carried out at least three times.

Prior to step b) and after step e) an additional step f) may be carried out, comprising f) distillation of organic composition (OC3) in a distillation column (D1), wherein i) an organic composition (OC4) is obtained from the upper part of (D1) and (OC4) comprises at least one alkane, at least one olefin and a reduced amount of at least one oligomerized olefin compared to the respective amount in (OC3), e use of (OC4) rather than (OC3) in the subsequent steps, a stream (S3) is obtained from the lower part of (D1) and (S3) comprises at least 80% by weight, preferably at least 95% by weight of the at least one oligomerized olefin present in organic composition (OC3).

The organic composition (OC4) may comprise at least 20 wt-% alkane, preferably butane, and less than 5 wt.-% oligomerized olefin, preferably octene.

Any distillation column known to the person skilled in the art being appropriate for performing the distillation in step f) and/or step g) (as defined below) may be employed.

Prior to step b) an additional step g) may be carried out, comprising
- g) distillation of organic composition (OC2), or optionally of organic composition (OC3) or optionally of organic composition (OC4) in a distillation column (D2), wherein
  - i) an organic composition (OC2a) is obtained from the upper part of (D2) and (OC2a) comprises at least one alkane and an reduced amount of at least one olefin compared to the respective amount in (OC2), (OC3) or (OC4), with use of (OC2a) rather than (OC2), (OC3) or (OC4) in the subsequent steps,
  - ii) a stream (S4) is obtained from the lower part of (D2) and (S3) comprises at least 80% by weight, preferably at least 90% by weight of the olefins present in (OC2), (OC3) or (OC4), preferably step e) is carried out prior to step f), step f) is followed by step g) and step g) is followed by step b).

In a preferred embodiment of the process according to the present invention, distillation column (D1) and/or distillation column (D2) serve the purpose of removing iso-butane and the respective organic composition fed into (D1) and/or (D2) comprises butane and/or butene.

Preferably distillation in step g) is carried out at temperatures at the upper part of distillation column (D2) ranging from 50 to 90° C., more preferably from 60 to 80° C. and most preferably from 65 to 75° C. and/or temperatures at the lower part of the distillation column (D2) ranging from 60 to 110° C., more preferably from 70 to 100° C. and most preferably from 80 to 90° C.

Preferably distillation in step g) is carried out at pressures at the lower part of distillation column (D2) from 8 to 15 bar, more preferably from 9 to 13 bar and most preferably from 10 to 12 bar. The pressure drop over the entire column can be, for example 0.1 to 0.5 bar.

Preferred columns employed as distillation column (D2) may be both packed columns and/or columns having built-in column trays (tray columns) and/or columns comprising both packing and trays, beds of packing elements in parts of the column and appropriate internals (steel plates) in other parts. Preferably the tray column comprises 40 to 150, more preferably 80 to 120 trays.

Preferably the distillation column (D2) comprises at least 5, more preferably at least 10 theoretical plates. Preferably the distillation column comprises a total number of theoretical plates from 10 to 100, more preferably from 20 to 100, most preferably from 30 to 100 and in a particular preferred embodiment 40 to 70.

In preferred embodiment, the distillation column (D2) is divided into a stripping section and an enrichment section; preferably the stripping section comprises 25 to 40 theoretical plates and the enrichment section comprises 15 to 30 theoretical plates.

Organic composition (OC2a) comprises preferably at least 96 wt-% butane and not more than 4 wt-% butane.

FIGURES

FIG. 1 illustrates certain aspects of the invention. For the sake of clarity not all applicable components and embodiments are drawn in one and/or all figures. Embodiments shown in different figures may be combined with each other and do not exclude the incorporation of further components within the limits of the disclosure of the specification.

FIG. 1 illustrates the most basic assembly of the present invention. Organic composition (OC1) is fed into adsorber (A1), run in operation mode, in order to obtain an organic composition (OC2) comprising at least one alkane, at least one olefin and a reduced amount of at least one compound containing oxygen and/or sulphur compared to the respective amount in organic composition (OC1). At least a part of the organic composition (OC2) is subsequently fed into the hydrogenation reactor (HR) and a stream (S2) is obtained, which is fed into adsorber (A2) run in regeneration mode. After a regeneration/purification cycle is finished, the adsorbers are operated in the respective other mode. Organic composition (OC1) is fed into an adsorber only in operation mode, while stream (S2) is fed only into an adsorber in regeneration mode.

Figure 2:
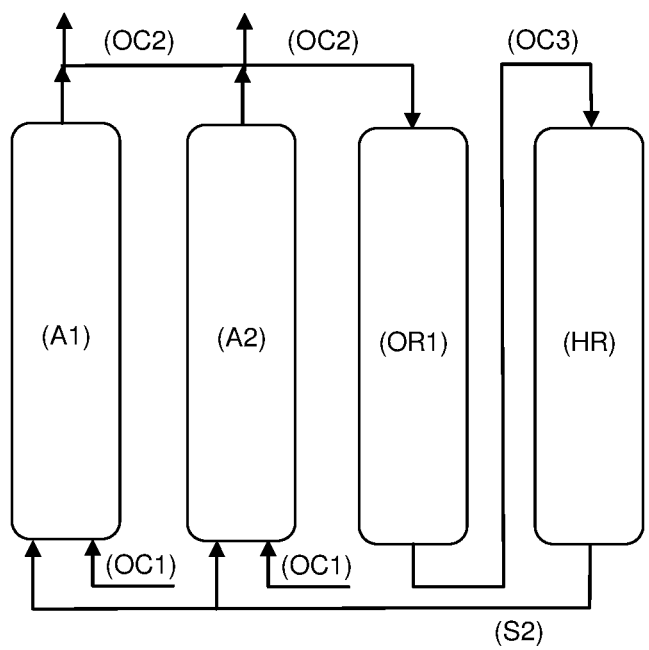

FIG. 2 shows a further embodiment of the invention, wherein organic composition (OC2) is fed into an oligomerization reactor (OR1) to obtain a stream (OC3) comprising a reduced amount of at least one olefin and an increased amount of at least one oligomerized olefin compared to the respective amounts in (OC2). Organic composition (OC3) is fed into the hydrogenation reactor (HR) instead of organic composition (OC2).

Figure 3:
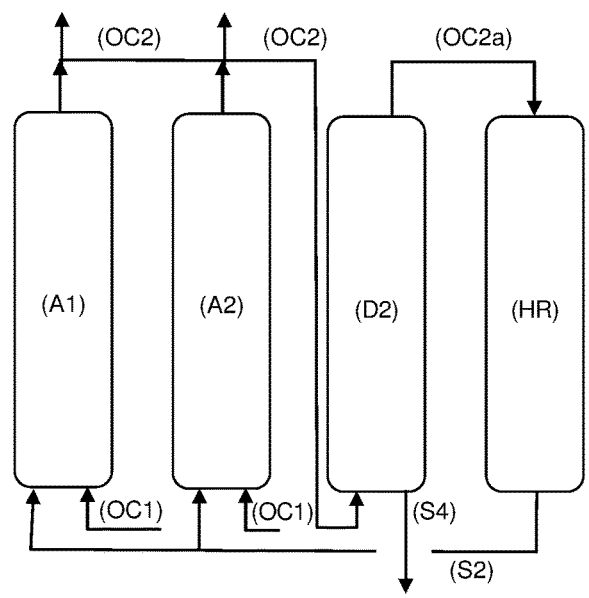

FIG. 3 demonstrates that the organic composition (OC2) may be subjected to a distillation in a distillation column (D2) to obtain from the upper part of (D2) an organic composition (OC2a) comprising at least one alkane and a reduced amount of at least one olefin compared to organic composition (OC2) as well as from the lower part of (D2) a stream (S4) comprising at least 80% by weight, preferably at least 90% by weight of the olefins present in organic composition (OC2). Organic composition (OC2a) is fed into hydrogenation reactor (HR) instead of organic composition (OC2).

Figure 4:
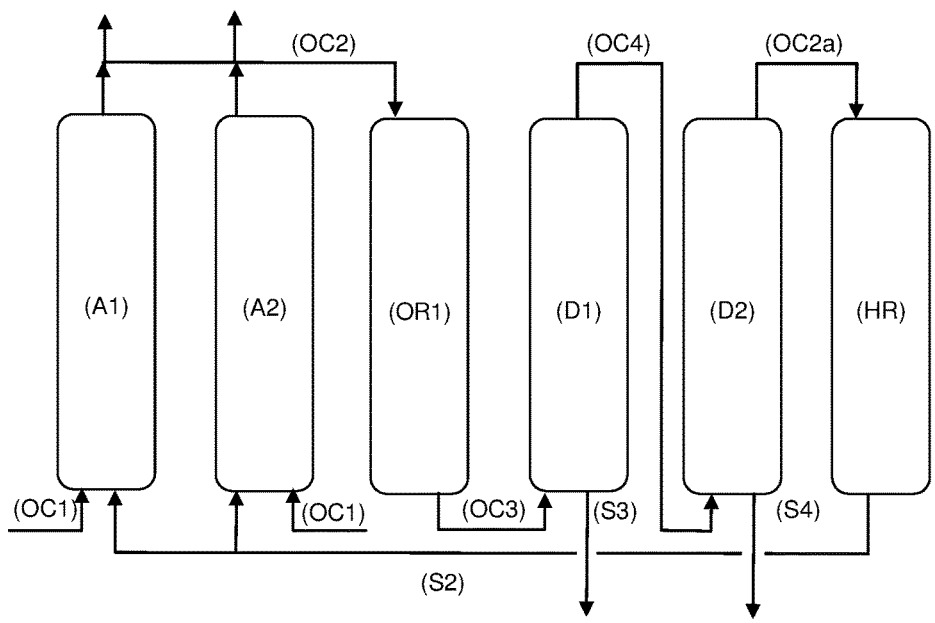

FIG. 4 illustrates an extension of the embodiment, shown in FIG. 2. Instead of being fed into the hydrogenation reactor (HR), organic composition (OC3) is passed through distillation column (D1) to obtain from the upper part of (D1) an organic composition (OC4) comprising at least one alkane, at least one olefin and a reduced amount of at least one oligomerized olefin compared to the respective amount in (OC3) and (OC2). Besides (OC4), from the lower part of (D1) a stream (S3) is obtained comprising at least 80% by weight, preferably at least 95% by weight of the at least one oligomerized olefin present in organic composition (OC3). (OC4) is fed into distillation column (D2) yielding from the upper part of (D2) organic composition (OC2a) comprising at least one alkane and a reduced amount of at least one olefin compared to organic composition (OC2), (OC3) or (OC4) and from the lower part of (D2) a stream (S4) comprising at least 80% by weight, preferably at least 90% by weight of the olefins present in (OC2) (OC3) or (OC4).

The invention claimed is:
1. A process, comprising:
   a) purifying an organic composition (OC1) comprising at least one alkane, at least one olefin, and at least one compound comprising oxygen or sulphur by feeding the organic composition (OC1) into a first adsorber (A1) of an assembly comprising at least two adsorbers arranged in parallel, to obtain an organic composition (OC2) comprising the at least one alkane, the at least one olefin, and a reduced amount of the at least one compound comprising oxygen or sulphur compared to the respective amount in the organic composition (OC1);
b) hydrogenating at least a part of the organic composition (OC2) obtained in step a) to obtain a stream (S2) comprising the at least one alkane and a reduced amount of the at least one olefin compared to the respective amount in the organic composition (OC2),
c) regenerating a second adsorber (A2) of the assembly by contact with the stream (S2) obtained in step b),
wherein the purifying step a) and the regenerating step c) are performed in parallel, and
wherein, in the organic composition (OC1), a weight ratio of the at least one alkane to the at least one olefin is 0.5:1 to 2:1.

2. The process according to claim 1, wherein
i) the organic composition (OC2) subjected to the hydrogenating step b) comprises butane and butene, or
ii) the organic composition (OC2) subjected to the hydrogenating step b) comprises ≤20 wt-ppm of at least one compound comprising oxygen or sulphur, or
iii) the stream (S2) comprises not more than 1000 wt-ppm olefin, or
iv) the stream (S2) comprises at least 99 wt-% of at least one alkane, or
v) the stream (S2) comprises ≤20 wt-ppm of at least one compound comprising oxygen or sulphur, or
vi) a load of the adsorber (A1) with the organic composition (OC1) in step a) is 10 to 100 t/h, or
vii) the organic composition (OC1) is fed into the adsorber (A1) in step a) at a temperature of 25 to 40° C., or
viii) the organic composition (OC1) is fed into the adsorber (A1) in step a) at a pressure of 5 to 8 bar.

3. The process according to claim 2, wherein
i) the at least a part of the organic composition (OC2) subjected to the hydrogenating step b) comprises at least 96 wt-% butane and not more than 4 wt-% butene, or
ii) the stream (S2) compromises at least 99 wt-% of butane.

4. The process according to claim 1, wherein the organic composition (OC1) comprises at most 1000 wt-ppm of at least one compound comprising oxygen or sulphur.

5. The process according to claim 1, wherein the organic composition (OC1) comprises butane and butene.

6. The process according to claim 1, wherein the at least two adsorbers (A1) and (A2) comprise a molecular sieve or aluminium oxide as the adsorbent, or the at least two adsorbers (A1) and (A2) adsorb compounds comprising oxygen or sulphur.

7. The process according to claim 6, wherein the at least two adsorbers (A1) and (A2) adsorb ethers, alcohols, thiols, thioethers, sulfoxides, ketones, aldehydes, or a mixture thereof.

8. The process according to claim 1, wherein the purifying step a) and the regenerating step c) are performed for the same period of time.

9. The process according to claim 1, wherein the period of time ranges from 12 to 48 h.

10. The process according to claim 1, wherein the regenerating step c) comprises:
c1) converting the stream (S2), which is liquid, into a gaseous phase;
c2) heating the second adsorber (A2) by contact with stream (S2), which is gaseous, wherein the gaseous stream (S2) is condensed within the second adsorber (A2) to obtain a condensate;
c3) further heating the second adsorber (A2) by contact with the stream (S2), which is gaseous, up to a temperature of 230 to 270° C. without any condensation of the gaseous stream (S2) within the second adsorber (A2);
c4) regenerating the second adsorber (A2) at a temperature of 230 to 270° C. by contact with the stream (S2), which is gaseous; and then
c5) cooling the second adsorber (A2) by contact with
the stream (S2), which is gaseous, to a temperature of 80° C. to 120° C.,
the stream (S2), which is liquid, obtained in step b) to a temperature of below 80° C., or
the stream (S2), which is gaseous, to a temperature of 80° C. to 120° C., and then the stream (S2), which is liquid, obtained in step b) to a temperature of below 80° C.

11. The process according to claim 10, wherein the regenerating step c) comprises the converting step c1), in which the conversion is carried out by employing at least one evaporator or at least one superheater or at least one flash vessel.

12. The process according to claim 1, further comprising:
a step d) prior to step c), wherein step d) comprises at least partially removing an organic composition that is formed in the second adsorber (A2) during its operation mode.

13. The process according to claim 12, wherein the regenerating step c) comprises:
c1) converting the stream (S2), which is liquid, into a gaseous phase;
c2) subsequently heating the second adsorber (A2) by contact with the gaseous stream (S2), wherein the gaseous stream (S2) is condensed within the second adsorber (A2) to obtain a condensate;
c3) subsequently heating the second adsorber (A2) by contact with the gaseous stream (S2) up to a temperature of 230 to 270° C. without any condensation of the gaseous stream (S2) within the second adsorber (A2);
c4) subsequently regenerating the second adsorber (A2) at a temperature of 230 to 270° C. by contact with the gaseous stream (S2);
c5) subsequently cooling the second adsorber (A2) by contact with the gaseous stream (S2) to a temperature of 80° C. to 120° C.; and
c6) subsequently cooling the second adsorber (A2) by contact with the liquid stream (S2) obtained in step b) to a temperature of below 80° C.

14. The process according to claim 13, comprising the step c2), wherein the condensate obtained in step c2) comprises the stream (S2) and a residue of the organic composition (OC1) or the organic composition (OC2) which was not removed from the adsorber (A2) when carrying out a draining step d), and the condensate is optionally collected in a device, and the collected condensate is passed through an adsorber during its operation mode.

15. A process, comprising:
a) purifying an organic composition (OC1) comprising at least one alkane, at least one olefin, and at least one compound comprising oxygen or sulphur by feeding the organic composition (OC1) into a first adsorber (A1) of an assembly comprising at least two adsorbers arranged in parallel, to obtain an organic composition (OC2) comprising the at least one alkane, the at least one olefin, and a reduced amount of the at least one compound comprising oxygen or sulphur compared to the respective amount in the organic composition (OC1);
b) carrying out an oligomerization of the organic composition (OC2), in which the at least one olefin is at least partially oligomerized, to obtain an organic composition (OC3) comprising a reduced amount of the at least one olefin and an increased amount of at least one oligomerized olefin compared to the respective amounts in the organic composition (OC2);
c) hydrogenating at least a part of the organic composition (OC3), to obtain a stream (S2) comprising the at least one alkane and a reduced amount of the at least one olefin compared to the respective amount in the organic composition (OC3); and
d) regenerating a second adsorber (A2) of the assembly by contact with the stream (S2) obtained in step c);
wherein the purifying step a) and the regenerating step d) are performed in parallel, and wherein, in the organic composition (OC1), a weight ratio of the at least one alkane to the at least one olefin is 0.5:1 to 2:1.

16. The process according to claim 15, wherein the oligomerization is a dimerization.

17. The process according to claim 16, wherein the at least one olefin is butene, which is at least partially dimerized to octene.

18. A process, comprising:
a) purifying an organic composition (OC1) comprising at least one alkane, at least one olefin, and at least one compound comprising oxygen or sulphur by feeding the organic composition (OC1) into a first adsorber (A1) of an assembly comprising at least two adsorbers arranged in parallel, to obtain an organic composition (OC2) comprising the at least one alkane, the at least one olefin, and a reduced amount of the at least one compound comprising oxygen or sulphur compared to the respective amount in the organic composition (OC1);
b) carrying out an oligomerization of the organic composition (OC2), in which the at least one olefin is at least partially oligomerized, to obtain an organic composition (OC3) comprising a reduced amount of at least one olefin and an increased amount of an at least one oligomerized olefin compared to the respective amounts in the organic composition (OC2);
c) distilling the organic composition (OC3) in a distillation column (D1) to obtain
  (i) an organic composition (OC4) from an upper part of the distillation column (D1), wherein the organic composition (OC4) comprises the at least one alkane, the at least one olefin, and a reduced amount of the at least one oligomerized olefin compared to the respective amount in the organic composition (OC3); and
  (ii) a stream (S3) from a lower part of the distillation column (D1), wherein the stream (S3) comprises at least 80% by weight of the at least one oligomerized olefin in the organic composition (OC3);
d) hydrogenating at least a part of the organic composition (OC4), to obtain a stream (S2) comprising the at least one alkane and a reduced amount of the at least one olefin compared to the respective amount in the organic composition (OC4); and
e) regenerating a second adsorber (A2) of the assembly by contact with the stream (S2) obtained in step d),
wherein the purifying step a) and the regenerating step e) are performed in parallel, and
wherein, in the organic composition (OC1), a weight ratio of the at least one alkane to the at least one olefin is 0.5:1 to 2:1.

19. A process, comprising:
a) purifying an organic composition (OC1) comprising at least one alkane, at least one olefin, and at least one compound comprising oxygen or sulphur by feeding the organic composition (OC1) into a first adsorber (A1) of an assembly comprising at least two adsorbers arranged in parallel, to obtain an organic composition (OC2) comprising the at least one alkane, the at least one olefin, and a reduced amount of the at least one compound comprising oxygen or sulphur compared to the respective amount in the organic composition (OC1);
b) distilling the organic composition (OC2) in a distillation column (D2) to obtain
  (i) an organic composition (OC2$a$) from an upper part of the distillation column (D2), wherein the organic composition (OC2$a$) comprises the at least one alkane and a reduced amount of the at least one olefin compared to the respective amount in the organic composition (OC2); and
  (ii) a stream (S4) from a lower part of the distillation column (D2), wherein the stream (S4) comprises at least 80% by weight of the olefins present in the organic composition (OC2);
c) carrying out an oligomerization of the organic composition (OC2$a$), in which the at least one olefin is at least partially oligomerized, to obtain an organic composition (OC3) comprising a reduced amount of at least one olefin and an increased amount of an at least one oligomerized olefin compared to the respective amounts in the organic composition (OC2$a$);
d) distilling the organic composition (OC3) in a distillation column (D1) to obtain
  (i) an organic composition (OC4) from an upper part of the distillation column (D1), wherein the organic composition (OC4) comprises the at least one alkane, the at least one olefin, and a reduced amount of the at least one oligomerized olefin compared to the respective amount in the organic composition (OC3); and
  (ii) a stream (S3) from a lower part of the distillation column (D1), wherein the stream (S3) comprises at least 80% by weight of the at least one oligomerized olefin in the organic composition (OC3)
e) hydrogenating at least a part of the organic composition (OC4), to obtain a stream (S2) comprising the at least one alkane and a reduced amount of the at least one olefin compared to the respective amount in the organic composition (OC4); and
f) regenerating a second adsorber (A2) of the assembly by contact with the stream (S2) obtained in step e),
wherein the purifying step a) and the regenerating step f) are performed in parallel, and
wherein, in the organic composition (OC1), a weight ratio of the at least one alkane to the at least one olefin is 0.5:1 to 2:1.

20. The process according to claim 19, wherein
the distillation column (D1) or the distillation column (D2) serve the purpose of removing iso-butane, and
the respective organic composition fed into (D1) or (D2) comprises butane or butene.

* * * * *

UNITED STATES PATENT AND TRADEMARK OFFICE
CERTIFICATE OF CORRECTION

PATENT NO. : 10,807,018 B2
APPLICATION NO. : 15/517558
DATED : October 20, 2020
INVENTOR(S) : Wagner et al.

Page 1 of 2

It is certified that error appears in the above-identified patent and that said Letters Patent is hereby corrected as shown below:

On the Title Page

Column 1, Item (72), in "Inventors", Line 6, delete "Wang (DE);" and insert -- Wan (CN); --, therefor.

Column 1, Item (51), under "Int. Cl.", Lines 1-2,
    *B01D 15/00*    (2006.01)
delete "*C10G 15/00*    (2006.01)" and insert -- *B01D 15/00*    (2006.01) --, therefor.

On Page 2, Column 1, Item (57), under "ABSTRACT", Line 4, delete "stream" and insert -- the stream --, therefor.

On Page 2, Column 1, Item (51), under "Int. Cl.", Lines 1-9,
    *C10G 25/12*    (2006.01)
    *C10G 57/02*    (2006.01)
    *C10G 45/00*    (2006.01)
    *C10G 25/00*    (2006.01)
    *C10G 67/06*    (2006.01)
    *C10G 69/12*    (2006.01)
    *B01D 3/14*    (2006.01)
    *C07C 2/06*    (2006.01)
delete "*C07C 5/03*    (2006.01)".

In the Specification

In Column 2, Line 36, delete "in over" and insert -- over --, therefor.

In Column 5, Lines 14-15, delete "mercaptane." and insert -- mercaptan. --, therefor.

In Column 9, Line 22, delete "spacial" and insert -- special --, therefor.
In Column 10, Line 64, delete "e use" and insert -- with the use --, therefor.

Signed and Sealed this
                              Second Day of March, 2021

Drew Hirshfeld
*Performing the Functions and Duties of the*
*Under Secretary of Commerce for Intellectual Property and*
*Director of the United States Patent and Trademark Office*

In Column 11, Line 16, delete "an reduced" and insert -- a reduced --, therefor.

In Column 12, Line 56, delete "(OC2)" and insert -- (OC2), --, therefor.

In the Claims

In Column 15, Claim 18, Line 42, delete "of at" and insert -- of the at --, therefor.

In Column 15, Claim 18, Line 43, delete "an at" and insert -- at --, therefor.

In Column 16, Claim 19, Line 32, delete "of at" and insert -- of the at --, therefor.

In Column 16, Claim 19, Line 33, delete "an at" and insert -- at --, therefor.